US009629647B2

(12) United States Patent
Smith et al.

(10) Patent No.: US 9,629,647 B2
(45) Date of Patent: Apr. 25, 2017

(54) ADJUSTABLE RESECTION DEVICE AND RELATED METHODS OF USE (71) Applicants: Paul Smith, Smithfield, RI (US); Samuel Raybin, Marlborough, MA (US)

(72) Inventors: Paul Smith, Smithfield, RI (US); Samuel Raybin, Marlborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 195 days.

(21) Appl. No.: 13/727,345

(22) Filed: Dec. 26, 2012

(65) Prior Publication Data

US 2013/0165959 A1 Jun. 27, 2013

Related U.S. Application Data (60) Provisional application No. 61/580,360, filed on Dec. 27, 2011.

(51) Int. Cl.
*A61B 1/00* (2006.01)
*A61B 17/32* (2006.01)
(Continued)

(52) U.S. Cl.
CPC .. *A61B 17/320016* (2013.01); *A61B 1/00089* (2013.01); *A61B 2017/00269* (2013.01); *A61B 2017/00336* (2013.01); *A61B 2017/00818* (2013.01); *A61B 2017/306* (2013.01); *A61B 2090/033* (2016.02)

(58) Field of Classification Search
CPC ........ A61B 17/320016; A61B 1/00089; A61B 2017/00269; A61B 2017/306; A61B 2017/00818; A61B 2017/00336; A61B 2019/303; A61B 1/00091; A61B 1/00064;
(Continued)

(56) References Cited

U.S. PATENT DOCUMENTS 4,219,013 A * 8/1980 Okada ................ A61B 1/00089 396/17
5,002,042 A * 3/1991 Okada ................ A61B 1/00089 600/127

(Continued)

FOREIGN PATENT DOCUMENTS

EP 1985250 A2 10/2008
GB 2365340 A 2/2002
(Continued)

OTHER PUBLICATIONS

International Search Report for corresponding international application PCT/US2012/071676, mailed Jul. 4, 2013, 6 pages.

*Primary Examiner* — Ryan J Severson
*Assistant Examiner* — Christian Knauss
(74) *Attorney, Agent, or Firm* — Bookoff McAndrews, PLLC (57) ABSTRACT A medical device and related method of use for resecting a tissue. The medical device may include an elongate member having a proximal end, a distal end, and a lumen extending therebetween. The elongate member may include a distal portion defining a cavity having an opening. In addition, a mechanism may be configured to adjust a volume of the cavity by altering a depth of the cavity.

7 Claims, 7 Drawing Sheets (51) Int. Cl.
*A61B 17/00* (2006.01)
*A61B 17/30* (2006.01)
*A61B 90/00* (2016.01)

(58) Field of Classification Search
CPC ............ A61B 1/00094; A61B 1/00101; A61B 2090/033
USPC ......... 600/101, 104, 106; 606/110, 111, 112, 606/113, 114, 115
See application file for complete search history.

(56) References Cited

U.S. PATENT DOCUMENTS

| | | | | |
|---|---|---|---|---|
| 5,976,073 | A * | 11/1999 | Ouchi | 600/129 |
| 6,042,591 | A * | 3/2000 | Mears | A61B 17/12013 606/140 |
| 6,306,081 | B1 | 10/2001 | Ishikawa et al. | 600/127 |
| 7,488,292 | B2 * | 2/2009 | Adachi | 600/504 |
| 7,507,200 | B2 * | 3/2009 | Okada | 600/104 |
| 7,588,580 | B2 * | 9/2009 | Okada | 606/113 |
| 2002/0035311 | A1 * | 3/2002 | Ouchi | 600/175 |
| 2002/0038125 | A1 * | 3/2002 | Hamilton | A61B 17/22031 606/115 |
| 2004/0034278 | A1 * | 2/2004 | Adams | 600/127 |
| 2005/0033276 | A1 * | 2/2005 | Adachi | A61B 1/04 606/32 |
| 2005/0043584 | A1 * | 2/2005 | Nozue | 600/127 |
| 2005/0080411 | A1 * | 4/2005 | Ouchi | A61B 18/1492 606/45 |
| 2005/0137453 | A1 * | 6/2005 | Ouchi et al. | 600/106 |
| 2006/0025654 | A1 * | 2/2006 | Suzuki et al. | 600/114 |
| 2006/0135849 | A1 * | 6/2006 | Adams | 600/104 |
| 2006/0200176 | A1 * | 9/2006 | Matsuno et al. | 606/140 |
| 2007/0118166 | A1 * | 5/2007 | Nobis et al. | 606/170 |
| 2008/0058586 | A1 * | 3/2008 | Karpiel | A61B 1/00089 600/104 |
| 2008/0300460 | A1 * | 12/2008 | Sugita | 600/127 |
| 2009/0198212 | A1 * | 8/2009 | Timberlake et al. | 604/506 |
| 2010/0191052 | A1 * | 7/2010 | Surti | A61B 1/00087 600/106 |
| 2011/0245679 | A1 | 10/2011 | Yamakita | |
| 2012/0041259 | A1 * | 2/2012 | McLawhorn | 600/106 |
| 2013/0110109 | A1 * | 5/2013 | Nguyen | A61B 17/32056 606/46 |

FOREIGN PATENT DOCUMENTS

JP 2000/79086 A 3/2000
WO WO 2011/126109 A1 10/2011

* cited by examiner

ADJUSTABLE RESECTION DEVICE AND RELATED METHODS OF USE

CROSS-REFERENCE TO RELATED APPLICATIONS

This application claims the benefit of priority from U.S. Provisional Application No. 61/580,360, filed Dec. 27, 2011, which is herein incorporated in its entirety.

FIELD OF THE INVENTION

This disclosure relates generally to systems and methods for resecting tissue. More particularly, embodiments of the present disclosure relate to minimally-invasive systems for endoscopic mucosal resection.

BACKGROUND OF THE INVENTION

Organ walls are composed of several layers: the mucosa (the surface layer), the submucosa, the muscularis (muscle layer), and the serosa (connective tissue layer). In gastrointestinal, colonic, and esophageal cancer, e.g., small polyps or cancerous masses may form along the mucosa and often extend into the lumens of the organs. Conventionally, that condition is treated by cutting out a portion of the affected organ wall. This procedure, however, may cause extensive discomfort to patients, and poses health risks. Recently, physicians have adopted a minimally invasive technique called endoscopic mucosal resection (EMR), which removes the cancerous or abnormal tissues (polyps), keeping the walls intact.

In some cases, EMR may be performed with an endoscope, which may be a long, narrow elongate member equipped with a light, video camera, and other instruments. During EMR, the endoscope is passed down the throat or guided through the rectum to reach an abnormality in the affected organ. In some procedures, the EMR device is further equipped with a dissection device such as a wire loop, which is passed through an endoscopic channel extending up to the cap towards the polyp. Once there, suction is applied to the elongate member, which draws the polyp towards the endoscope cap. When the polyp is sufficiently drawn into the cap, the wire loop closes around the polyp, resecting it from the organ wall. Alternatively, a band may be placed around the tissue to accomplish resection or necrostasis. Subsequently, excised tissue may be extracted for examination, biopsy, or disposal. The tissue or polyp cauterization process may be accomplished by any know cautery or dissection tool.

Certain polyps, such as pedunculated polyps, are characterized by a stalk attached to the mucosal layer. Drawing such polyps into the cap without drawing in any other tissue is readily accomplished. Certain other polyps, such as sessile polyps, however, exhibit a broad base and they lay flat on the mucosal surface, devoid of a stalk. It is often difficult to grasp these polyps without drawing in a part of the muscularis layer.

In addition, the depth of the cut made by a wire loop cautery is critical. As discussed above, if the cut is too deep, the muscularis layer may be injured, which may cause a perforation. Conversely, if the cut is too shallow, the procedure may not remove enough of the affected tissue, which can require additional procedures, or worse, result in the development of metastatic cancer. Typically, more than 2 mm of cancer clearance is required to assure complete removal. EMR, as performed with conventional devices and methods, may result in complications such as perforation, bleeding, and/or strictures.

Therefore, there exists a need for an improved endoscopic mucosal resection tool that effectively resects both pedunculated and sessile polyps without damaging the surrounding tissue or muscle layers of the organ.

SUMMARY OF THE INVENTION

Embodiments of the present disclosure relate to a medical device for resecting an undesired mass from a patient's body using a minimally invasive surgical system.

In accordance with an aspect of the present disclosure, the medical device includes an elongate member having a proximal end, a distal end, and a lumen extending therebetween. The elongate member include a distal portion defining a cavity having an opening. In addition, a mechanism may be configured to adjust a volume of the cavity by altering a depth of the cavity.

In various embodiments, the medical device may include one or more of the following additional features: the distal portion may be a hood coupled to the elongate member; the mechanism may include a sleeve, extending distally from the elongate member, movable relative to the elongate member; the mechanism may be a limiter disposed within the distal portion; the distal end of the limiter may be substantially parallel to the opening in the hood; the mechanism may be an elongate suction tube extending from a working channel of the elongate member; the hood may be removably coupled to the distal end of elongate member; the mechanism may be configured to slidably move a portion of the hood relative to a distal end of the elongate member; the proximal end of the hood may include a base, which may be fixedly or slidably attached to the inner surface of the hood; a second mechanism configured to pull tissue into the cavity; a vacuum within the cavity; and a lock for fixing the length of the cavity.

According to another embodiment, the medical device may include an elongate member having a proximal end, a distal end, and a lumen extending therebetween. A hood may be coupled to a distal portion of the elongate member, the hood defining a cavity configured to receive tissue. In addition, a limiter may be configured to selectively control a volume of tissue received in the hood.

In various embodiments, the medical device may include one or more of the following additional features: the hood may be removably coupled to the distal portion of the elongate member; the limiter may be a base slidably attached to the inner surface of the hood; the limiter may include an elongate member extending distally from within the elongate member and disposed within the cavity, wherein a length of the limiter in the cavity is adjustable; the limiter may be a suction tube; the medical device may further include a lock for selectively fixing a position of the limiter; the limiter may be configured to move between first and second positions within the cavity; the limiter may be a separate component for the end user to select and install; the medical device may further include a mechanism for pulling the tissue into the hood; and the suction source may be in communication with the limiter.

A further aspect of the present disclosure includes a method for resecting tissue. The method may include advancing a resection device to a desired location proximate a bodily wall. The resection device may include an elongate member having a proximal end, a distal end, and a lumen extending therebetween. The elongate member may also include a distal portion defining a cavity having an opening and a mechanism configured to adjust the volume of the cavity by varying the depth of the cavity. The method may further include adjusting the depth of the cavity, drawing the tissue on the bodily wall into the hood, and excising the tissue.

Additional objects and advantages of the claimed invention will be set forth in part in the description which follows, and in part will be obvious from the description, or may be learned by practice of the claimed invention. The objects and advantages of the claimed invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to systems and methods for resecting and extracting tissue including cancerous, foreign, or undesirable tissue from a patient's body. For example, the device may remove cancerous polyps or lesions from the mucosal walls of the colon, esophagus, stomach, or duodenum. A physician may also desire to resect tissue in order to conduct a biopsy or other examination. It should be understood that the resection device may perform the functions of both resecting and retrieving, but for convenience, the term "resection device" will be used throughout this application.

The resection device may include a hood fitted on the distal end of any suitable elongate member, such as an endoscope, for ensnaring, band ligating, cauterizing/severing, and extracting tissue such as a polyp. The hood may fit on other suitable devices such as guide tube or introducer device. The hood provides a cavity for capturing the undesired tissue or polyp using suction and subsequently, a conventional cautery or other dissecting device may resect the tissue just beyond the distal end of the hood. To avoid damaging the underlying tissue layer, the embodiments of the present disclosure employ an adjustable depth limiter whose axial position within the hood determines the depth of tissue drawn into the hood.

The adjustable limiter may be an elongate member that extends through a working channel of the endoscope. The limiter may extend into the hood so that it's distal end limits the depth of tissue that can be drawn into the hood. Alternatively, the hood may itself be movable on the endoscopic elongate member such that a depth of the hood beyond the distal end of the endoscope may vary. The depth of the hood beyond the distal end of the endoscope controls the tissue volume drawn into the hood. In an alternate embodiment, instead of the hood the elongate member includes a sleeve extending from the distal end and the length of the sleeve beyond the distal end defines a cavity for resecting polyps. The length of the sleeve beyond the elongate member's distal end may be adjustable.

In the following sections, embodiments of the present disclosure will be described using an exemplary body organ—the stomach. The embodiments of resection device discussed below aim to remove a lesion on the mucosal layer of the stomach without damaging the underlying muscularis layer. It will be understood that the stomach is merely exemplary and that the device may be utilized in any other suitable organ, and in particular the gastrointestinal tract, such as the colon, duodenum, esophagus, or any other organ that may be subject to polyps, lesions, or at any location where tissue may be resected or biopsied.

Exemplary Embodiments

Figure 1:
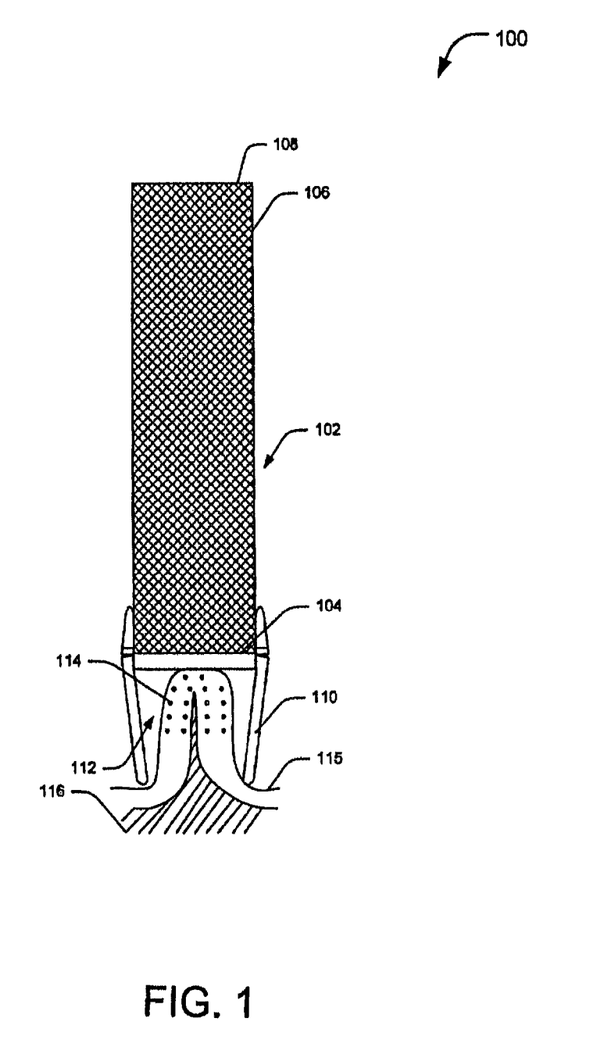
FIG. 1 is cross-section view of an embodiment of a conventional resection device.

FIG. 1 is a view of an embodiment of a resection device 100 for resecting polyps, lesions, or other tissue from the walls of an organ. The resection device 100 includes an elongate member 102 having a proximal end 106, distal end 104, and a lumen 108 extending between the proximal and distal ends 106, 104. Proximal end 106 may be coupled to a handle (not shown), while distal end 104 is coupled to a hood 110.

Elongate member 102 may be an endoscope or other flexible or rigid introduction device adapted to be advance into a body lumen. In the illustrated embodiment, elongate member 102 may include one or more channels (not shown), through which, the operator may introduce one or more medical devices to extend out of the distal end of elongate member 102. For example, during a resectomy, the operator may introduce a suction device into one channel, and a snare loop into another. Additionally, from time to time during the procedure, the operator may insert a light source, a camera, an injector, or a morcellator within the channel. Further, a ligation band may be passed through the channel. As discussed below in greater detail, the ligation band (or any suitable device) may be configured to promote necrostasis when applied to tissue. Elongate member 102 may be any known endoscopic device used for colonoscopy, resectoscopy, cholangioscopy, or mucosal resection, and thus, this device will not be discussed in greater detail.

Hood 110 may be a relatively short, generally tubular member configured to be fitted over the distal end of elongated member 102. The distal end of hood 110 defines a cavity 112, having an opening. In the illustrated embodiment, the opening is substantially perpendicular to the longitudinal axis of the elongate member, creating a distally facing opening. In other embodiments, however, the distal end of hood 110 may be cut at an angle to the longitudinal axis, creating a tapered tip. The slanted distal tip provides for greater surface area contact between the hood's distal end and the targeted tissue. In addition, hood 110 is uniformly cylindrical in shape, but where required by given applications, the hood 110 may describe an elliptical, semi-circular, rhombic, or rectangular profile. Moreover, the diameter of the hood 110 may vary based on the size of the body lumens in which it operates. For example, a distal portion of hood 110 may be tapered relative to a proximal portion of hood 110.

Any suitable material may be used to fabricate the hood 110. For instance, rigid or semi-rigid materials such as metals (including super elastic materials such as Nitinol), polymers, resins, or plastics may be used. In some embodiments, the distal end of hood 110 may be made of a flexible material while the remaining portion may be rigid. Alternatively, only the proximal end may be flexible. Flexible ends may allow the hood 110 to form a seal with the contacting tissue and the elongate member 102. Hood 110 may also be optically clear, allowing physician to visualize tissue disposed within the hood. Further, a biocompatible material that does not irritate the body lumens may be applied as a coating over the outer surface of hood 110. The coating may also prevent blood or other tissue from depositing and adhering to hood's surface. In some embodiments, the walls of hood 110 may include a plurality of channels and/or openings. These channels and/or openings may be used to facilitate the delivery of suction to an interior of hood 110.

In addition, outer surface of the hood 110 may include markings. For example, radiopaque or sonoreflective markings (not shown) may be added to an exterior surface of the hood 110. For example, the distalmost edge of hood 110 may be radiopaque or sonoreflective. These markings facilitate detection of a position and/or orientation of the hood 110 within the patient's body, and a surgeon, with the aid of suitable imaging equipment, may track the path followed by the endoscope system and avoid potential damage to sensitive tissues. Further, hood 110 may have radiopaque material disposed within it's walls. In other embodiments, the material that hood 110 is made of may be radiopaque itself In use, the resection device 100 draws tissue 114, such as a lesion formed on the mucosal layer 115 that is located above the muscularis layer 116, into the cavity 112. Any known tissue-drawing mechanism may accomplish this task. Although the embodiments of the present disclosure employ a suction device, various other known devices may be contemplated such as pincers, baskets, forceps, and corkscrews. The suction is provided through a working channel (not shown) of the elongate member 102. With lesion 114 drawn into cavity 112, as shown in FIG. 1, the operator extends a dissecting device such as a blade, scissor, snare, cautery, or laser device, through another working channel of the endoscope and severs the lesion 114. In some embodiments, these dissection devices may also be introduced along the outer surface of the elongate member 102. For example, a dissection device may be independently introduced through, e.g., another introduction device, to the dissecting plane.

During this process, the depth of the tissue pulled into the hood 110 determines the depth of the cut made by the cautery device. In general, only the lesion 114 should be drawn into the hood 110, allowing convenient removal. If cavity 112 is too deep, the suction force may also draw the underlying muscularis layer 116 into the hood 110 along with the lesion 114, as shown in FIG. 1. Severing the lesion 114 in such a state may perforate the muscularis layer 116, a potentially dangerous situation. Conversely, if the entire lesion 114 is not drawn into the hood 110, the resection device may not remove enough affected tissue. That situation may require additional procedures, or if undetected, it may lead to a metastasized cancer. Consequently, the depth of tissue drawn into the hood 110 is critical, and this depth varies based on the mucosal layer thickness. Conventionally, the amount of tissue drawn for resection is only dependent on the dimensions of the endoscopic device, such as the diameter, instead of the tissue thickness.

Embodiments of the present disclosure employ an adjustable mechanism that allows a user to control the amount of tissue drawn into the hood 110, also referred to as "suction depth", based on the thickness of the tissue layer. This adjustable mechanism may be embodied in a number of forms, all of which enable an operator to selectively control the volume of the cavity 112 based on the desired amount of mucosal layer to remove.

Figure 2A:
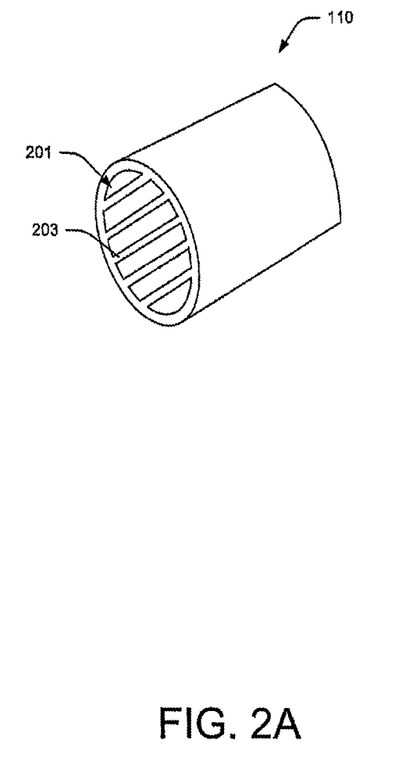
FIG. 2A illustrates a hood having depth adjustment capabilities according to embodiments of the present disclosure

FIG. 2A illustrates the hood 110 according to an embodiment of the present disclosure. As shown, hood 110 is similar in design and configuration to the one shown in FIG. 1. In addition, the proximal end of the hood 110 includes a grate 201 that may define a base for the hood 110.

In the illustrated embodiment, grate 201 includes multiple arms 203 disposed parallel at a distance to each other, forming a grid-like structure. Arms 203 may be made of suitable rigid material, such as metal, polymer, fiber. Grate 201 may be fixedly or slidably attached to a proximal end of the hood 110.

In one embodiment of the present disclosure, slidable grate 201 may slide along the inner surface of the hood 110 varying the hood's cavity size. Based on the tissue thickness, grate 201 may slide and fix on a desired position within the hood 110. The surface of the hood 110 may include radiopaque or suitable markings that may assist in measuring the tissue thickness drawn into the hood 110.

Various known mechanism may be used to vary the position of the grate 201. For example, grate 201 may be connected to pull wires that control the position of the grate from the proximal end of the elongate member 102. In one implementation, hood's inner surface may include projections or rails that may allow grate 201 to be fixed at varying positions. Alternatively, known span-fit connection, magnetic connections, or other known mechanism may also be contemplated.

In other embodiments, grate 201 may be fixed attached to the hood 110. In such implementation, the embodiments of the present disclosure may employ additional features to limit the tissue drawn into the hood 110. The following sections describe some of the tissue adjustable mechanism.

Figure 2B:
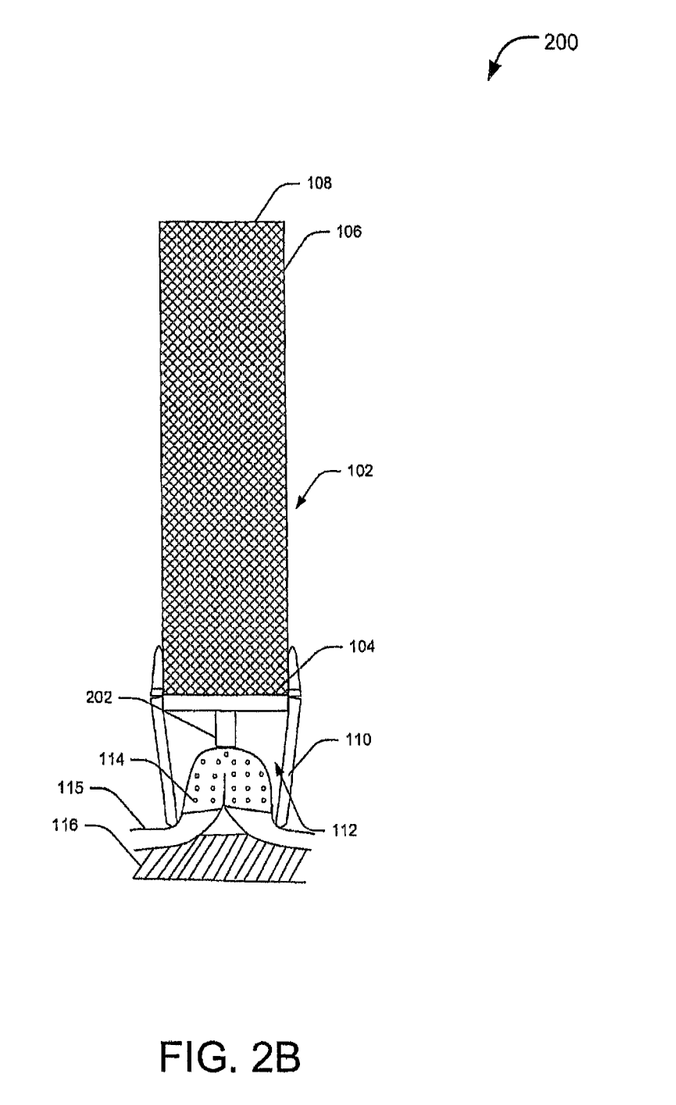
FIG. 2B illustrates a resection device having depth adjustment capabilities according to embodiments of the present disclosure.

FIG. 2B illustrates an embodiment of a resection device 200 that allows adjustable depth resection. Some of the elements depicted in FIG. 2B are similar to the embodiment shown in FIG. 1, such as the elongate member 102 and the hood 110. These elements operate in similar fashion here and thus require no further elaboration. In addition, the illustrated embodiment includes a limiter 202 that allows an operator to adjust the tissue volume drawn into the hood 110. Particularly, the limiter 202 may adjust the length of the cavity while the diameter of the cavity remains constant.

As shown, the limiter 202 may be a generally rigid elongate member retractably introduced through the elongate member 102. In general, the limiter 202 may be an elongate member, having a uniform configuration, introduced to the hood 110 through a working channel (not shown). Different configurations of the limiter 202 may be contemplated. In one embodiment, limiter 202 may be an elongate rod running along the length of the elongate member 102. The diameter of limiter 202 is selected to provide a sufficiently broad surface to limit the tissue being drawn into cavity 112. As can be understood, if limiter 202 is too thin, tissue will simply wrap around its distal end, defeating the purpose of the device 200. On the other hand, the diameter must be chosen with a view to operating within the normal working channel of elongate member 102. In some embodiments, the distal end of the limiter 202 may be wider than the proximal end to limit the tissue suction volume effectively. Alternatively, the distal end of the limiter 202 may be connected to a disc or any suitably shaped member that has a wider surface area. In addition, in some embodiments, limiter 202 may be a rod with length greater than or equal to the depth of the hood 110.

Different dimensions of the limiter 202 may be contemplated. In any configuration, however, the limiter 202 should be a rigid member made of suitable material, such as stainless steel, that can oppose the tissue drawn into the hood 110. In addition, the distal end of the limiter 202 may lie substantially parallel to the distal end of the hood 110 to limit the tissue volume drawn into the hood 110. Where required by given applications, the limiter 202 may include a disc, a cuboid, or a selectively expandable cage-like structure. In any configuration, however, the limiter 202 should be a rigid member made of suitable material, such as stainless steel, that can oppose the tissue drawn into the hood 110. In some embodiments, limiter 202 may not limit the tissue drawn into the hood 110, but may act as a ruler to measure the amount of tissue drawn.

The axial position of the limiter 202 within the hood 110 may be controlled using endoscopic device retraction mechanisms. For example, a user may push or pull limiter 202 from its proximal end. Alternatively, limiter 202 may run on rails 402 extending completely or partially along the length of elongate member 102. Alternatively, limiter 202 may not extend the entire length of elongate member 102, in which case it may be connected to pull wires (not shown) running along the length of the elongate member. A user may push or pull the wires to advance the limiter 202 within the hood 110 or retrieve it from the hood 110, respectively. In addition, any suitable actuation means may be used to selectively extend and/or retract limiter 202.

In one embodiment of the present disclosure, the inner surface of the hood 110 may include ridges or projections that may act as a ratchet to the limiter 202. For example, the distal end of the limiter 202 may include corresponding protrusions that may slide over the ratchets and fixed to the desired depth.

To fix the deployed position of the limiter 202, an embodiment of the present disclosure may utilize known locking mechanisms. For example, the outer surface of the limiter may include threads that can mate with corresponding grooves on the inner surface of an elongate member's channel. Alternatively, the limiter 202 may include projections to allow a snap fit attachment. In other embodiments, the limiter 202 may be connected to a spring at its proximal end in its compressed state, and one or more pull wires may hold the spring in any desired state. Releasing the pull wires expands the spring and consequently, the limiter 202 moves distally. Once the desired limited position is achieved, the pull wires may be fastened. Other known locking mechanisms to engage the limiter 202 securely with the elongate member 102 in a retractable fashion may be contemplated such as a magnetic connection.

The axial position of the limiter 202 within the hood 110 determines the depth of tissue drawn into the hood 110. In the situation illustrated in FIG. 2B, limiter 202 extends mid-way within the hood 110. This position allows tissue to occupy only the portion of cavity 112 distal of the tip of limiter 202. The thickness of the mucosal layer at any given location of the gastrointestinal tract can be accurately determined, and thus the operator can limit the amount of tissue resected by carefully positioning limiter 202.

Figure 3A:
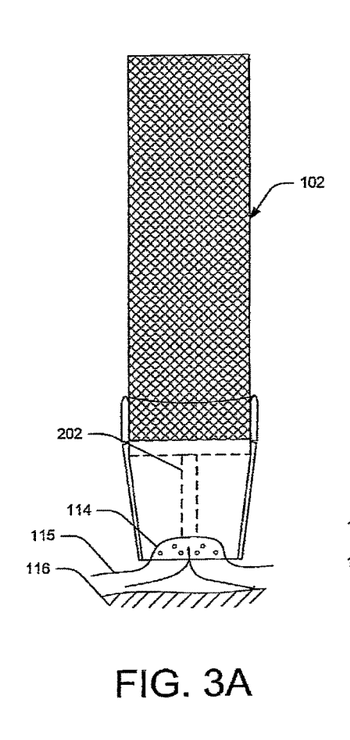
FIGS. 3A, 3B, and 3C illustrate three different axial positions of a limiter depicted in the resection device of FIG. 2B.
Figure 3B:
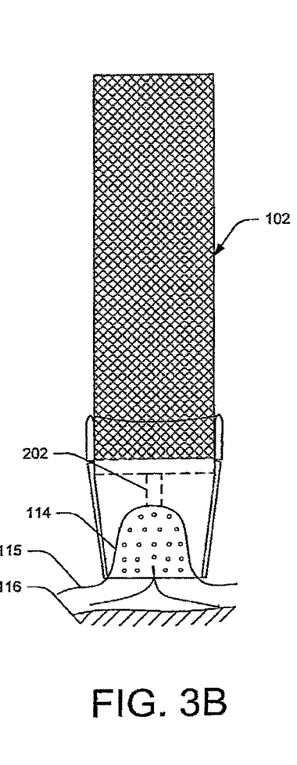
Figure 3C:
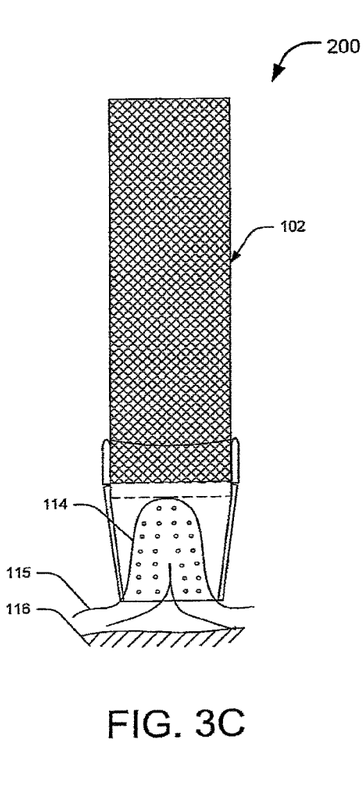

FIGS. 3A, 3B, and 3C depict three different axial positions of the limiter 202 within the hood 110. In FIG. 3A, the limiter 202 is advanced only slightly short of the distal end of hood 110, allowing only a limited amount of a tissue to enter the hood 110. In other instances where the limiter 202 is fully retracted within the elongate member, tissue can occupy the entire hood volume, as shown in FIG. 3C. With limiter 202 positioned anywhere between the two extreme positions tissue occupies the remaining amount of cavity 112, as shown in, e.g., FIG. 3B. In each illustration, the limiter position varies the effective cavity depth, which in turn controls the amount of tissue that can be drawn into hood 110. Adjusting the position of limiter 202, and thus the cavity depth, allows a user to only draw affected tissue into the hood 110, preventing unwanted excision of, e.g., healthy tissue.

Figure 4A:
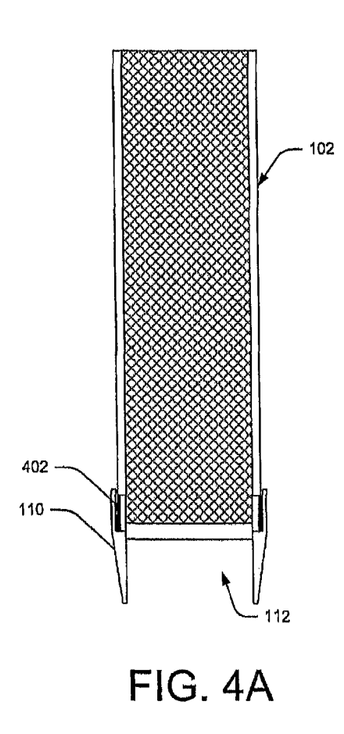
FIGS. 4A and 4B illustrate an alternate embodiment of a resection device, according to the principles of the disclosure.
Figure 4B:
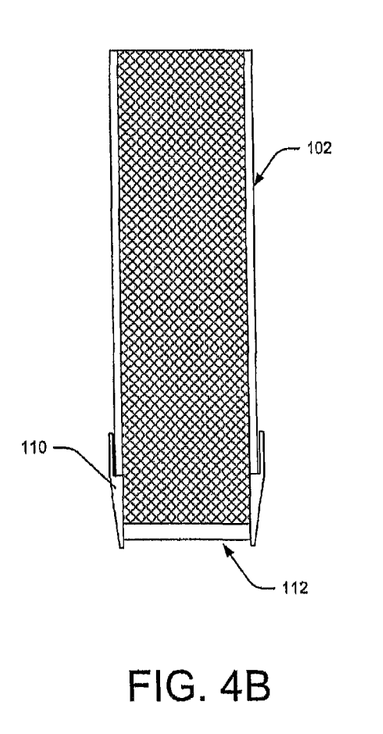

Alternatively, FIGS. 4A and 4B illustrate an embodiment in which the adjustable mechanism may be implemented as an adjustable hood. In contrast to previous embodiments in which the hood 110 may be fixedly attached to the elongate member 102, here the hood 110 is configured to slide back and forth at the distal end of elongate member 102. As shown, hood 110 may be positioned on rails 402 on the outer surface of the elongate member 102. Although any other suitable mechanism for removably fixing the hood 110 to the elongate member 102 may be utilized. The inner surface of the hood 110 may also include corresponding projections or grooves that facilitate the hood's traveling on rails 402.

FIG. 4A depicts a configuration where the hood 110 is extended distally, allowing maximum cavity volume for tissue suction. The opposite situation is shown in FIG. 4B, showing hood 110 fully retracted on rails 402. That configuration permits acquisition of only a limited amount of tissue. Hood 110 may attain any deployed position between the ones shown in FIGS. 4A and 4B. When the hood 110 attains the required cavity depth, the device 400 may also include a locking mechanism (not shown) to secure the hood's position relative to elongate member 102.

It will be understood that other techniques to retractably engage the hood with the elongate member 102 may be contemplated without departing from the scope of the present disclosure. For example, a span fit attachment or a magnetic connection may be possible between the hood 110 and elongate member 102. Other mechanical arrangements will be clear to those having ordinary skill in the art.

Figure 5:
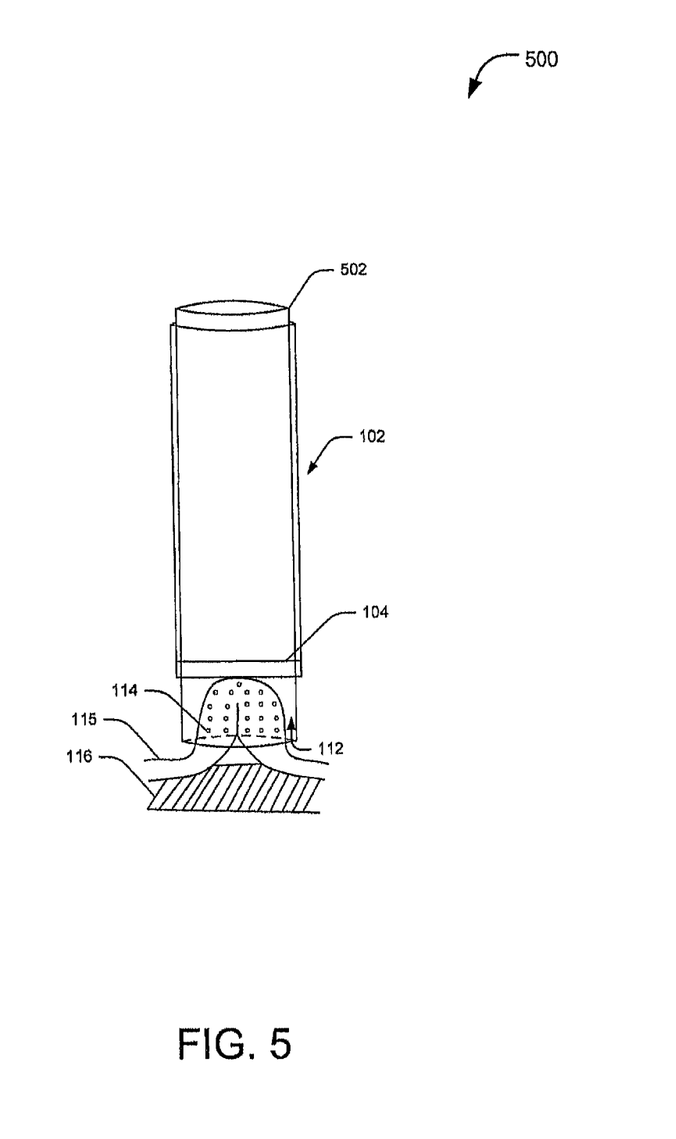
FIG. 5 illustrates a further embodiment of the resection device, according to the present disclosure.

Varying cavity length may be achieved using various other known mechanisms. FIG. 5 illustrates an embodiment in which the depth adjustable mechanism may be implemented using a retractable sleeve. In contrast to previous embodiments that employ hood 110 to define cavity 112 for the tissue resection, the present embodiment includes a sleeve 502 that includes a distally-facing opening, defining a cavity such as the cavity 112.

Sleeve 502 may be cylindrical member extending along the length of the elongate member 102 or extending from a distal end of the elongate member 102. Sleeve 502 may be an integral part of the elongate member or a separate device. Further, Sleeve 502 may be a rigid or semi-rigid structure. Alternatively, it may be accordion-like or similar structure having scaffolds. In each of the configuration, the diameter of the sleeve 502 may remain constant while the length may be adjustable. Extension of the sleeve 502 beyond the distal end of the elongate member 102 defines length of the cavity 112.

The length of the sleeve may be adjustable by known mechanism. For example, sleeve 502 may be extended/retracted from the proximal end manually or through control mechanism. If the sleeve 502 extends only a distal portion of the elongate members, the sleeve may be connected to pull wires extending up to the proximal end. Extension/retraction of sleeve 502 may be controlled by these pull wires. If sleeve 502 is an accordion-like device than expansion/compression of the structure may vary the length of the sleeve 502 extending beyond the distal end of the elongate member 102.

Sleeve 502 may be made of fiber or wires that may be woven or braided together using synthetic plastics, fiber, or polymers. Alternatively, sleeve 502 may be formed from materials such as stainless steel or the like, including super elastic alloys such as Nitinol. In general, sleeve 502 may be made of any suitable material that is biocompatible. Suitable materials may include nitinol, ePTFE, fabric, and suitable nickel and titanium alloys. Those in the art are well aware of the range of suitable and available materials.

Figure 6:
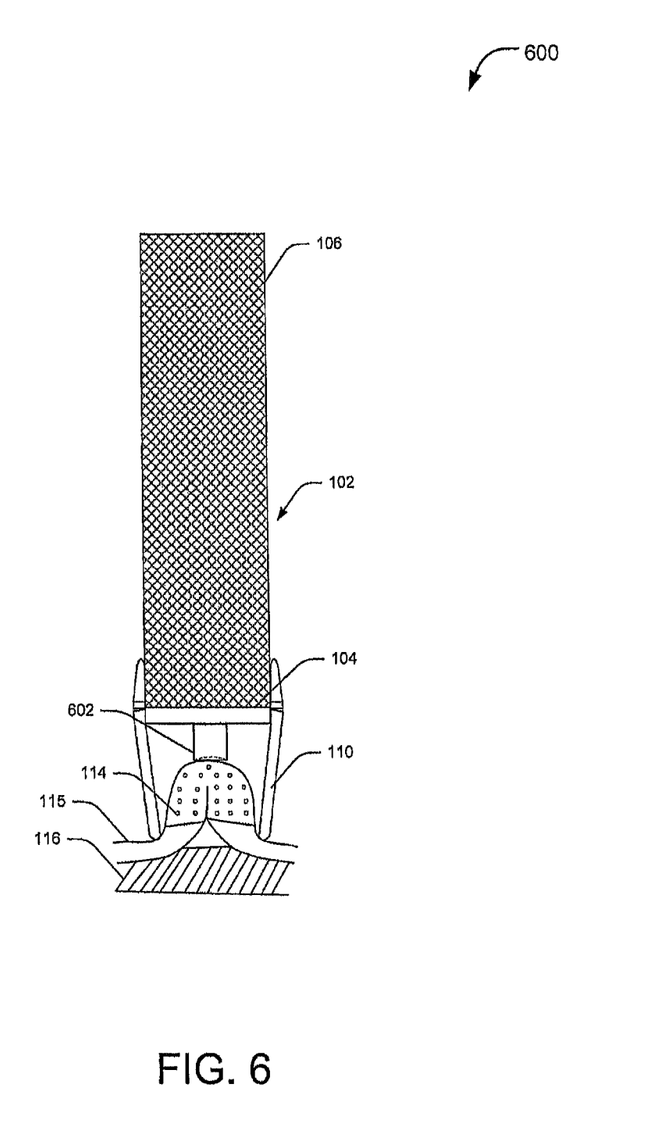
FIG. 6 illustrates a further embodiment of the resection device having a suction tube configured to draw tissue into the hood at a controlled depth according to embodiments of the present disclosure.

In another alternate embodiment, shown in FIG. 6, the limiter 202 may be configured as a suction tube 602. Here tube 602 is a hollow element connected to a suction source (not shown). This tube may extend the length of the elongate member 102, and it performs two functions—drawing tissue into the hood and controlling the amount of tissue drawn in. In a manner analogous to the functioning of the embodiment of FIG. 2B, tube 602 exerts suction to draw tissue up to the level of its distal tip. That tip can be positioned at any desired depth in the cavity 112.

The following section sets out an exemplary method for resecting lesions, polyps, or otherwise undesired tissue from a patient's body. A typical location for a resection of this sort is the stomach, and that location will be discussed here. As will be understood by those in the art, other patient locations would be equally suitable. Either a percutaneous incision is made to access the gastrointestinal tract, or the resection device 200 may be inserted through a natural opening, such as the mouth.

Once inserted, the resection device 200 is directed towards the lesion present on mucosal walls. A light source and a camera may be inserted in the working channel to direct the device within the stomach, and to identify the lesions. In other embodiments, however, suitable optical and imaging equipment may be integrated with resection device 200. To detect these lesions, a biomarker or dye may be sprayed around the gastrointestinal tract. Cancerous lesions emit a different wavelength when light falls on them, allowing operators to easily detect them. Other suitable methods or apparatus will be readily apparent to those having ordinary skill in the art.

Subsequently, if hood 110 includes an adjustable grate 201, then the position of the grate may be modified based on the thickness of tissue that needs resection. Alternatively, if the grate 201 is fixed to the hood 110, various depth adjustable mechanism may be employed. For example, a limiter such as the limiter 202, may be deployed. In the embodiment shown in FIG. 2B, elongate member 102 carries hood 110 on its distal end, with limiter 202 extending through a working channel. As explained above, limiter 202 is positioned within hood 110 at a depth calculated to resect the desired amount of mucosal layer 115 without perforating the muscularis layer 116. In an alternate embodiment, to limit the tissue depth resected by the device 200, the hood 110 may be retracted relative to elongate member 102 to control the cavity depth provided by the hood 110. In another embodiment, the sleeve 502 extending from the distal end may also be retracted relative to the elongate member 102 to define the required cavity 112.

Once the resection device 200 is positioned, a suction device (not shown) is applied to the working channel to draw tissue including the lesion 114 into cavity 112. If desired, the suction device may be powered off or removed, and a telescope or microscope may be introduced in the elongate member 102 along with a light device to closely examine the lesion 114 to determine whether the lesion requires resection. Various known techniques may be employed for this determination.

If resection is required, a cautery or other suitable dissection device such as a snare loop may be employed to remove tissue including lesion 114 from the mucosal wall 115. Other resecting means such as a laser device or a bander may be contemplated, which will lie within the scope of the present disclosure.

Once the lesion is resected, the device may carry out any one of a number of procedures to remove the resected tissue. For example, the resection device 200 may extract the resected tissue, or morcellate it and then extract it. For extraction, any retrieval device presently known or later developed may be employed. In one embodiment, the resected tissue may be extracted with the help of suction force applied at the proximal end of the resection device 200. In another embodiment, a basket, a grasper, forceps, or pincers may be used. In one implementation, the resection device 200 may include hemostasis devices to assist in healing the wound. Such devices may include, but are not limited to, ligating bands, RF electrodes, and/or hemostatic agents.

Embodiments of the present disclosure may be used in any medical or non-medical procedure, including any medical procedure where appropriate resection of an undesired body tissue is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A medical device comprising:
  a member having a proximal end, a distal end, and a lumen extending therebetween;
  a hood coupled to a distal portion of the member, the hood defining a distal-facing cavity configured to receive tissue; and a limiter configured to selectively control a volume of tissue received in the hood, the limiter including a distalmost surface configured to abut tissue to limit proximal movement of the tissue into the hood, wherein movement of the limiter controls the volume of tissue received by adjusting a length of the cavity without adjusting a diameter of the cavity, where the length of the cavity is measured from the distalmost surface of the limiter to a distalmost end of the hood, and wherein the limiter is disposed within the cavity and moves relative to a proximal end of the cavity, wherein the limiter includes a suction tube.

2. The medical device of claim 1, wherein the hood is removably coupled to the distal portion of the member.

3. The medical device of claim 1, wherein the limiter includes a second member extending distally from within the member and disposed within the cavity, wherein a length of the limiter in the cavity is adjustable.

4. The medical device of claim 1, further comprising a mechanism for pulling the tissue into the hood.

5. The medical device of claim 1, wherein pulling the limiter increases the volume of the tissue received.

6. The medical device of claim 1, wherein the limiter is configured so tissue received by the cavity is completely exterior to the limiter.

7. A method for resecting tissue, the method comprising:
advancing a resection device to a desired location proximate a bodily wall, the resection device comprising:
   a member having a proximal end, a distal portion, and a lumen extending therebetween;
   a hood coupled to the distal portion of the member, the hood defining a cavity having a distal-facing opening; and
   a limiter including a suction tube, wherein the limiter is configured to selectively control a volume of tissue received in the hood and includes a distalmost surface configured to abut tissue to limit proximal movement of the tissue into the hood, wherein movement of the limiter controls the volume of tissue received by adjusting a length of the cavity without adjusting a diameter of the cavity, where the length of the cavity is measured from the distalmost surface of the limiter to a distalmost end of the hood, and wherein the limiter is disposed within the cavity and moves relative to a proximal end of the cavity;
adjusting the length of the cavity by moving the limiter;
drawing tissue on the bodily wall into the hood; and
excising the tissue.

* * * * *